United States Patent [19]

Beck et al.

[11] Patent Number: 5,138,056
[45] Date of Patent: Aug. 11, 1992

[54] POLYCYANOPYRIMIDINES AND PROCESS FOR THEIR PREPARATION

[75] Inventors: Gunther Beck, Leverkusen; Ernst Kysela, Bergisch-Gladbach, both of Fed. Rep. of Germany

[73] Assignee: Bayer Aktiengesellschaft, Leverkusen, Fed. Rep. of Germany

[21] Appl. No.: 712,853

[22] Filed: Jun. 10, 1991

[30] Foreign Application Priority Data

Jun. 19, 1990 [DE] Fed. Rep. of Germany ....... 4019420

[51] Int. Cl.⁵ .................. C07D 239/30; C07D 239/28
[52] U.S. Cl. ...................................... 544/242; 544/334
[58] Field of Search ............................... 544/334, 242

[56] References Cited

PUBLICATIONS

Konno et al. in Heterocycles, vol. 26, No. 12, (1987) pp. 3259 et seq., p. 3264.
W. Klotzer in Mh. Chem. Bd. 87 (1956) pp. 527 et seq., p. 527.
Shkurko Chemical Abstracts, vol. 87, No. 21, Nov. 21, 1977, "Pyrimidines. LXII. Some reactions of pyrimidine cyano derivatives".
Morrison and Boyd, "Organic Chemistry" Allyn and Bacon, Boston, (1959) p. 441.

*Primary Examiner*—John M. Ford
*Attorney, Agent, or Firm*—Sprung Horn Kramer & Woods

[57] ABSTRACT

The invention relates to new polycyanopyrimidines of the formula

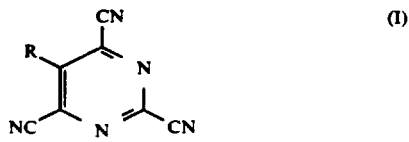

in which
  R represents chlorine or cyano,
and to a process for their preparation.

4 Claims, No Drawings

POLYCYANOPYRIMIDINES AND PROCESS FOR THEIR PREPARATION

The invention relates to new polycyanopyrimidines and to a process for their preparation.

New polycyanopyrimidines of the formula

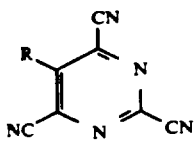
(I)

have been found in which

R represents chlorine or cyano.

The invention further relates to a process for the preparation of the polycyanopyrimidines of the formula (I); the process is characterised in that polyfluoropyrimidines of the formula

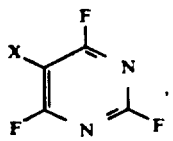
(II)

in which

X represents chlorine or fluorine, are reacted with alkali metal cyanides in organic diluents.

Alkali metal cyanides used are preferably the inexpensive cyanides of sodium or potassium.

The reaction with the alkali metal cyanides is carried out in organic diluents. Organic diluents employed are customary aprotic polar or dipolar solvents. Examples of such solvents are:

aliphatic nitriles such as acetonitrile, proprionitrile, 3-methoxy-propionitrile; aliphatic and cyclic ethers such as ethylene glycol dimethyl ether, diethylene glycol dimethyl ether (diglyme), tetrahydrofuran; N,N-dialkylamides of lower aliphatic carboxylic acids, such as N,N-dimethylformamide, N,N-dimethylacetamide or N-methylpyrrolidone; aliphatic sulphoxides such as dimethyl sulphoxide; aliphatic sulphones such as dimethyl sulphone and tetramethylene sulphone; and also tetramethylurea, N,N-dimethyl-1,3-imidazolidin-2-one and hexamethylphosphoric triamide. Acetonitrile and N,N-dimethylformamide are particularly preferred.

The reaction of the polyfluoropyrimidines of the formula (II) with the alkali metal cyanides can be carried out at temperatures from −70° C. to +50° C., preferably from −50° C. to +30° C., particularly preferably from −40° C. to +10° C.

The reaction is in general carried out at normal pressure.

The reaction according to the invention of the compounds of the formula (II) with the alkali metal cyanides can be described by the following reaction equations:

a) for the reaction to give 5-chloro-2,4,6-tricyanopyrimidine:

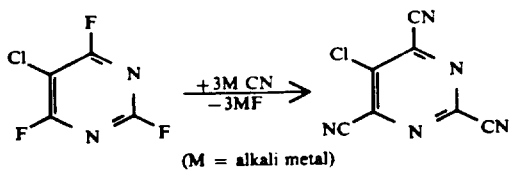
(M = alkali metal)

b) for the reaction to give tetracyanopyrimidine:

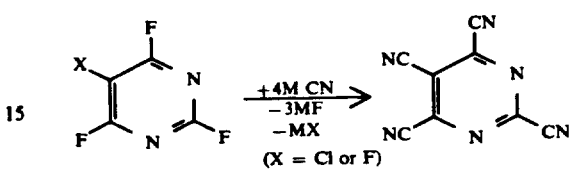
(X = Cl or F)

As can be seen from the above reaction equations (a) and (b), 3 or 4 mol of alkali metal cyanide per mole of starting compound (II) are required for the preparation of the polycyanopyrimidines of the formula (I) according to the invention.

For the preparation of 5-chloro-2,4,6-tricyanopyrimidine with contents of tetracyanopyrimidine which are as low as possible, not more than 3 mol of alkali metal cyanide are used per mole of 5-chloro-2,4,6-trifluoro-pyrimidine. When using the particularly preferred solvent or diluent dimethylformamide, reaction in a temperature range from −40° C. to −20° C. is particularly preferred.

It has been found that it can be advantageous to work with a subequivalent amount of alkali metal cyanides. The reaction according to the invention of polyfluoropyrimidines of the formula (II) with the alkali metal cyanides in fact proceeds, as can be detected with gas chromatographic monitoring of the reaction, via the intermediate steps of the isomeric monocyano-trihalogenopyrimidines, for example via 5-chloro-4-cyano-2,6- difluoro-pyrimidine and 5-chloro-2-cyano-4,6-difluoropyrimidine when using 5-chloro-2,4,6-trifluoropyrimidine as compound (II), and dicyano-dihalogeno-pyrimidines, for example 5-chloro-2,4-dicyano-6-fluoro-pyrimidine when using 5-chloro-2,4,6-trifluoropyrimidine as polyfluoropyrimidine of the formula (II) and for example 2,4-dicyano-5,6-difluoro-pyrimidine when using tetrafluoropyrimidine as polyfluoropyrimidine of the formula (II). The two last-mentioned dicyano-dihalogeno-pyrimidines can even be isolated by fractional sublimation. In spite of this, essentially only the polycyanopyrimidines of the formula (I) according to the invention are formed even when using a subequivalent amount of cyanide, and an amount of unreacted starting pyrimidine of the formula (II) corresponding to the subequivalent amount of cyanide remains behind.

For the preparation of tetracyanopyrimidine having a content of 5-chloro-2,4,6-tricyano-pyrimidine which is as low as possible from the 5-chloro-2,4,6-trifluoropyrimidine (II, X=Cl) preferably used as a starting material, 4 mol of alkali metal cyanide are preferably employed per mole of 5-chloro-2,4,6-trifluoro-pyrimidine; a temperature range of 0° C. to 20° C. has additionally proved particularly suitable when using the particularly preferred diluent dimethylformamide. On the other hand, if the reaction is carried out, for example, at temperatures between −30° C. and 0° C., mixtures of 5-chloro-2,4,6-tricyano-pyrimidine and tetracyanopyrimidine are obtained with reaction times between about 1 to 10 hours, it being possible, however, to separate the mixtures into their individual constituents, for example by chromatography, by recrystallisation or by fractional sublimation.

For the preparation of tetracyanopyrimidine from the starting material tetrafluoropyrimidine (II, X=F) which is accessible with difficulty and therefore not preferred, the reaction is particularly preferably carried out, in particular also with respect to its particularly high reactivity, in the lower part of the temperature range indicated. The use of a subequivalent amount (for example only 50% of the stoichiometrically required amount) of alkali metal cyanide is problem-free in this case, as it can easily be separated, for example by fractional sublimation, if desired with resultant 2,4-dicyano-5,6-difluoro-pyrimidine, owing to its easy volatility.

The starting materials of the formula (II) present unreacted in the reaction mixture when using a subequivalent amount of cyanide and/or a prematurely discontinued reaction are easily separable because of their considerably easier volatility compared with the polycyanopyrimidines of the formula (I) according to the invention and can be reused in the next batch.

It has been found that the polycyanopyrimidines of the formula (I) according to the invention are only obtained in medium to good yields if the polyfluoropyrimidines of the formula (II) are reacted with alkali metal cyanides under mild reaction conditions and alkali metal cyanides are used in not more than a small excess over the amount stoichiometrically required for the reaction. By means of the parameters "mild reaction conditions" and "not more than a small excess of alkali metal cyandies", the formation of undesired secondary products which, owing to the high reactivity of the polycyanopyrimidines of the formula (I), in particular of tetracyanopyrimidine, comes to the fore, is suppressed to such an extent that the desired polycyanopyrimidines of the formula (I) are still obtained in medium to good yields.

The invention therefore relates in particular to a process for the preparation of polycyanopyrimidines of the formula (I), which is characterised in that polyfluoropyrimidines of the formula (II) are reacted in organic diluents under mild reaction conditions with not more than an excess of 20%, preferably not more than an excess of 10% over the stoichiometrically required amount, of alkali metal cyanides.

The starting materials of the formula (II), 5-chloro-2,4,6-trifluoro-pyrimidine and tetrafluoropyrimidines, are well-known compounds, which in some cases are produced on an industrial scale.

The reaction according to the invention of the alkali metal cyanides with the compounds of the formula (II) is preferably carried out by adding the stoichiometrically required amount of alkali metal cyanide (or a subequivalent amount) to the solution of the polyfluoropyrimidine of the formula (II) in the anhydrous solvent concerned with exclusion of moisture and with stirring under mild conditions, i.e. at temperatures from −50° C. to −40° C. and additionally stirring vigorously in the selected final temperature range from −30° C. to +30° C., for example, for 1–10 hours. After completion (or premature discontinuation) of the reaction, the reaction mixture is in general added to excess (for example twice to 10 times the volume) of ice-water which at least contains a quantity of mineral acid, for example hydrochloric acid, such that the pH is <7 after stirring in the reaction solution. The polycyanopyrimidines of the formula (I) according to the invention are then isolated by filtration and subsequently purified if desired.

Polycyanobenzenes and polycyano(poly)aza-benzenes are important starting materials for the preparation of charge transfer complexes; these CT complexes are distinguished in some cases by very good electrical conductivity (see, for example, Bull. Acad. Polon. Sci. 23, 563 (1975); dissertation by Peter Neumann, University of Freiburg im Breisgau, FRG, 1968; Synthetic Metals 19, page 415 (1987)). The polycyanopyrimidines of the formula (I) synthesised for the first time here give, for example with pyrene, deeply dark-coloured charge transfer complexes having interesting material properties. The polycyanopyrimidines of the formula (I) in some cases moreover have biocidal effects, in particular insecticidal and fungicidal effects.

EXAMPLE 1

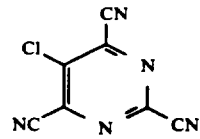

14.7 g (0.3 mol) of sodium cyanide are added in portions at about −40° C. with stirring and with exclusion of moisture to the solution obtained from 16.85 g (0.1 mol) of 5-chloro-2,4,6-trifluoro-pyrimidine in 170 ml of dry dimethylformamide. The reaction mixture is stirred at −25° C. to −20° C. for 6 hours. It is then poured with stirring into a mixture of 550 g of ice and 300 ml of 1-normal aqueous hydrochloric acid. After the ice has melted, the resulting precipitate is filtered off, washed with water and dried to constant weight.

11.10 g of solid product are obtained, which is sublimed up to a bath temperature of 200° C. at 0.1 mbar. Sublimation residue: 1.35 g. According to gas chromatographic analysis, the sublimate consists of pure 5-chloro-2,4,6-tricyano-pyrimidine without any content of tetracyanopyrimidine. Yield of sublimed 5-chloro-2,4,6-tricyanopyrimidine 51.4 % of theory. Melting point 167°–168° C. (from cyclohexane or from 1,2-dichloroethane).

IR (KBr) in cm$^{-1}$: 2261, 2250, 1529, 1352, 1194, 1089, 947, 920, 873, 788.

EXAMPLE 2

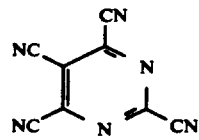

98.0 g (2 mol) of sodium cyanide are added in portions at about −40° C. with stirring and with exclusion of moisture to the solution obtained from 84.25 g (0.5 mol) of 5-chloro-2,4,6-trifluoro-pyrimidine in 850 ml of dry dimethylformamide. The temperature of the reaction mixture is then allowed to rise to +5° C. in the course of about one hour and it is then stirred at +5° C. to +10° C. for a further 6 hours. The reaction mixture is then stirred into a mixture of 2.3 kg of ice-water and 2 liters of 1-normal hydrochloric acid while maintaining the same temperature. The resultant precipitate is immediately filtered off, washed with ice-water and dried.

43.40 g of solid product are obtained, which is sublimed up to a bath temperature of 200° C. at 0.1 mbar. Sublimation residue: 13.71 g. According to gas chromatographic analysis, the sublimate consists of pure tetracyanopyrimidine without any content of 5-chloro-2,4,6-tricyanopyrimidine. Yield of sublimed tetracyanopyrimidine 33.0 % of theory. Melting point 190°-191° C. (from dichloromethane or from 1,2-dichloroethane).

IR (KBr) in cm$^{-1}$: 2246, 1539, 1526, 1381, 934, 800, 702.

EXAMPLE 3

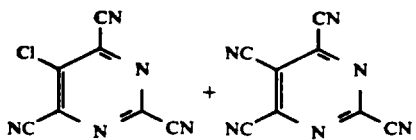

The procedure is as described in Example 2, the difference being that the reaction mixture is stirred at −25° C. to −20° C. for 6 hours after completion of NaCN addition. The reaction is worked up as described in Example 2; 50.3 g of solid product are obtained, which is sublimed up to a bath temperature of 200° C. at 0.1 mbar. Sublimation residue: 3.47 g. According to gas chromatographic analysis, the sublimate consists to 56.1% of 5-chloro-2,4,6-tricyano-pyrimidine and to 43.7% of tetracyanopyrimidine. The total yield of sublimed cyanopyrimidines is about 50% of theory.

Example 4

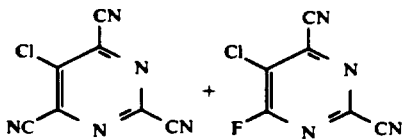

66.15 g (1.35 mol) of sodium cyanide is added in portions at −50° C. to −40° C. with stirring and with exclusion of moisture to the solution obtained from 84.25 g (0.5 mol) of 5-chloro-2,4,6-trifluoro-pyrimidine in 850 ml of dry dimethylformamide. The temperature of the reaction mixture is then allowed to rise to −30° C. in the course of about half an hour and it is then stirred at −30° C. to −25° C. for a further 6 hours. The reaction mixture is stirred into a mixture of 2.85 kg of ice-water and 1.35 liters of 1-normal hydrochloric acid while maintaining the temperature of −30° C. to −25° C.; the resultant precipitate is filtered off, washed with water and dried.

57.60 g of solid product are obtained, which is sublimed up to a bath temperature of 180° C. at 0.1 mbar. Sublimation residue: 7.78 g. According to gas chromatographic analysis, the sublimate consists to 98.2% (corresponding to 51.6% of theory) of 5-chloro-2,4,6-tricyano-pyrimidine and to 1.8% of 5-chloro-2,4-dicyano-6-fluoropyrimidine. The latter compound is distinctly more easily volatile than the principal product and is therefore deposited separately from the principal product during the sublimation in a position in the sublimation apparatus which is further removed from the heating mantle than the position in which the principal product is deposited Melting point of 5-chloro-2,4-dicyano-6-fluoro-pyrimidine after recrystallising from cyclohexane: 108° to 110° C. (in a closed tube).

After recrystallising the entire sublimate, for example from 1,2-dichloroethane, pure 5-chloro-2,4,6-tricyanopyrimidine is obtained.

IR (KBr) in cm$^{-1}$ from 5-chloro-2,4-dicyano-6-fluoropyrimidine: 2264, 2252, 1547, 1392, 1340, 1200, 1026, 921, 779, 700.

GC conditions:

Column: OV 1701, 20 m, 0.5 mbar helium prepressure
Programme: 100° C.-10° C./min-300° C. detected using FID

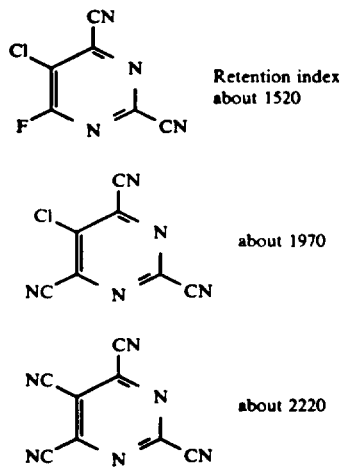

EXAMPLE 5

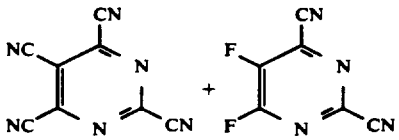

7.35 g (0.15 mol) of sodium cyanide are added at −55° C. to −50° C. with stirring and with exclusion of moisture to the solution obtained from 7.60 g (0.05 mol) of tetrafluoropyrimidine in 100 ml of dry dimethylformamide. The internal temperature is then allowed to rise to −35° C. and the mixture is then vigorously stirred for a further 4 hours in a temperature range from −35° C. to −30° C. The crude mixture is stirred into a mixture of 850 g of ice-water and 150 ml of 1N hydrochloric acid without further warming, and the resultant precipitate is immediately filtered off, washed with ice-water and dried. The solid product principally consists of tetracyanopyrimidine; the small amounts of 2,4-dicyano-5,6-difluoro-pyrimidine contained in the solid product can be isolated by fractional sublimation to 120° C./0.1 mbar. Melting point 104° C.

IR (KBr) in cm$^{-1}$ from 2,4-dicyano-5,6-difluoro-pyrimidine: 2259, 1578, 1437, 1419, 1199, 1009, 932, 804, 780, 707.

We claim:

1. Polycyanopyrimidines of the formula

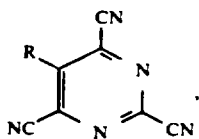

in which

R represents chlorine or cyano.

2. Process for the preparation of polycyanopyrimidines of the formula

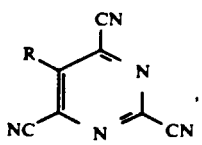

in which

R represents chlorine or cyano, characterised in that polyfluoropyrimidines of the formula

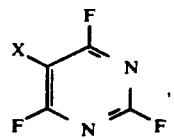

in which

X represents fluorine or chlorine,
are reacted with alkali metal cyanides in organic diluents.

3. Process according to claim 2, characterised in that the reaction is carried out with not more than a small excess over the stoichiometrically required amount of alkali metal cyanide.

4. Process according to claim 2, characterised in that the reaction is carried out at temperatures from $-50°$ C. to $+30°$ C. using the stoichiometrically required amount or a subequivalent amount of alkali metal cyanide.

* * * * *